United States Patent [19]
Jia et al.

[11] Patent Number: 6,013,694
[45] Date of Patent: Jan. 11, 2000

[54] DENTAL COMPOSITES COMPRISING GROUND, DENSIFIED, EMBRITTLED GLASS FIBER FILLER

[75] Inventors: Weitao Jia, Wallingford; Martin L. Schulman, Orange; Arun Prasad, Cheshire; Bruce Alpert, Madison, all of Conn.

[73] Assignee: Jeneric/Pentron Incorporated, Wallingford, Conn.

[21] Appl. No.: 08/951,414

[22] Filed: Oct. 16, 1997

[51] Int. Cl.$^7$ ................ C08K 3/40; A61K 6/08
[52] U.S. Cl. ............ 523/116; 523/115; 524/450; 524/494; 501/69; 65/33.1; 65/33.7; 65/442
[58] Field of Search ............... 523/115, 116; 501/69; 524/450, 494; 65/33.1, 33.7, 442

[56] References Cited

U.S. PATENT DOCUMENTS

| | | |
|---|---|---|
| 2,477,268 | 7/1949 | Saffir . |
| 2,514,076 | 7/1950 | Kelly . |
| 3,096,144 | 7/1963 | Wainer et al. . |
| 3,328,230 | 6/1967 | Levecque et al. . |
| 4,215,033 | 7/1980 | Bowen . |
| 4,381,918 | 5/1983 | Ehrnford . |
| 4,392,828 | 7/1983 | Ehrnford . |
| 4,427,799 | 1/1984 | Orlowski et al. . |
| 4,500,657 | 2/1985 | Kumar ........................ 523/117 |
| 4,514,174 | 4/1985 | Dougherty et al. . |
| 4,707,504 | 11/1987 | Walkowiak et al. . |
| 4,717,341 | 1/1988 | Goldberg et al. . |
| 4,731,394 | 3/1988 | Vogel et al. . |
| 4,744,759 | 5/1988 | Bowen . |
| 4,793,809 | 12/1988 | Sigler et al. . |
| 4,894,012 | 1/1990 | Goldberg et al. . |
| 4,952,530 | 8/1990 | Brosnan et al. . |
| 4,997,373 | 3/1991 | Tanaka et al. . |
| 5,078,596 | 1/1992 | Carberry et al. . |
| 5,081,164 | 1/1992 | Lai . |
| 5,084,491 | 1/1992 | Kerby . |
| 5,266,609 | 11/1993 | Hall et al. . |
| 5,378,737 | 1/1995 | Jacobs et al. . |
| 5,549,123 | 8/1996 | Okuyama et al. . |
| 5,621,035 | 4/1997 | Lyles et al. . |
| 5,676,745 | 10/1997 | Kelly et al. . |
| 5,788,499 | 8/1998 | Hoffman . |

FOREIGN PATENT DOCUMENTS 2 416 074  8/1979  France .

OTHER PUBLICATIONS

DentsplyCaulk, *Sure Fill, High Density Posterior Restorative, Technical Manual,* pp. 1–23.

K.F. Leinfelder et al, *A New Polymer Rigid Matrix Material,* CDA Journal, Sep. 1996, pp. 78–82.

*Primary Examiner*—Andrew E. C. Merriam
*Attorney, Agent, or Firm*—Cantor Colburn LLP

[57] ABSTRACT

A composite for a dental restoration is presented comprising ground, densified, embrittled glass fibers together with fillers and a polymeric matrix precursor composition. The ground, densified, embrittled glass fibers are obtained by grinding glass fibers which have been densified and embrittled by heating glass fibers at a temperature substantially below the softening point of the glass fibers, without significant fusion or melting together of the fibers. The composite is particularly useful as a direct filling material, in that it has the feel and workability of an amalgam.

48 Claims, 2 Drawing Sheets

DENTAL COMPOSITES COMPRISING GROUND, DENSIFIED, EMBRITTLED GLASS FIBER FILLER

BACKGROUND OF THE INVENTION

1. Field of the Invention

This invention relates to dental composite materials and methods of manufacture thereof In particular, this invention relates to improved glass fiber fillers for dental composite materials, wherein the glass fibers are densified and embrittled by heating the fibers.

2. Brief Discussion of the Related Art

Compositions useful for repairing damaged teeth in situ are known in the art as direct filling materials, and include alloys and resin composites. Dental amalgam alloys have widely been used as direct filling material, and provide excellent handling characteristics, and physical properties. The technique of mechanically packing and condensing a material into a tooth cavity is previously known to the dental profession in connection with the use of dental amalgams as a direct filling material. It has well known advantages in that it permits a close adaptation of the filling material to the cavity walls and also makes it possible to make firm contacts between the restored tooth and its neighbor. Further, it makes it possible to give the restoration its final anatomic form before hardening, thereby avoiding the time consuming and difficult finishing work with rotating instruments required with composite materials. These advantages are the densified, embrittled glass fiber composites on the present invention and the method of manufacture thereof However, there are perceived health hazard concerns regarding the use of high amounts of mercury or gallium present in amalgam alloys.

Dental resins have accordingly been developed, which comprise polymeric matrices, for example polyamides, polyesters, acrylates, polyolefins, polyimides, polyarylates, polyurethanes, vinyl esters, or epoxy-based materials. Other polymeric matrices include styrenes, styrene acrylonitriles, ABS polymers, polysulfones, polyacetals, polycarbonates, polyphenylene sulfides, and the like. The most popular polymeric matrices are based on monomers having at least one ethylenically unsaturated group, in particular acrylate and methacrylate groups. One commonly used monomer of this class is the reaction product of bisphenol A with glycidyl methacrylate (hereinafter BIS-GMA). In addition, these resins have also been used to make artificial teeth and denture basis.

Unfilled (i.e., pure) curable acrylic and methacrylic resins generally suffer from polymerization shrinkage and poor durability. These drawbacks have been reduced in direct filling applications, in part, through the addition of inert fillers. See, for example, U.S. Pat. No. 3,066,112 which is herein incorporated by reference. The combination of binder plus filler is commonly referred to as a composite direct filling material. Currently used fillers for curable dental resins generally are inert materials in the form of finely divided irregular particles, fibers or beads, present in an amount from about 35 to about 80 percent by weight of the total composite direct filling material.

Commonly used inorganic fillers include fused silica, quartz, glass, various mineral silicates (e.g., β-eucryptite, lepidolite, petalite, spondumene, beryl, topaz and zircon), silicon carbide, alumina, and mixtures thereof Commonly-assigned U.S. Pat. No. 4,544,359 to Waknine, for example, discloses a filler mixture comprising barium silicate, borosilicate glass, and colloidal silica. In general composite direct filling materials which are fully loaded with inorganic fillers (i.e. combined with the highest workable volume loading) having particles in the range of 0.01–1.2 microns are the most wear-resistant currently available composite direct filling materials. However, these composite direct filling materials containing finely divided inorganic fillers and acrylic binder resins may not polish as easily as unfilled dental resin.

Organic materials have also been used as fillers. For example, U.S. Pat. No. 3,923,740 discloses a direct filling material containing finely divided cured polymethyl methacrylate, alone or in conjunction with an inorganic filler. Composite direct filling materials which are wholly or partly filled with finely divided polymethyl methacrylate have better polishability (i.e. better surface finish after polishing with ordinary dental tools) than composite direct filling materials which are fully loaded with inorganic fillers, but generally have poorer durability (i.e. poorer wear resistance in vivo) than composite direct filling materials having inorganic fillers only.

Regarding fibrous fillers in particular, U.S. Pat. No. 2,477,268 to Saffir discloses short glass fibers randomly dispersed in dental resin materials, as does U.S. Pat. No. 2,514,076 to Kelly. Use of long, fully wetted fibers in structural components for dental restorations and the like are disclosed in U.S. Pat. Nos. 4,894,102 to Goldberg et al. However, none of these patents is discloses a composite having the feel of amalgam.

Fused-fibrous filler compositions in the dental arts are also known. Such fused fibrous fillers are of particular interest because they reportedly provide a feel similar to that of amalgam when used by the dentist, and may be applied using similar techniques. In U.S. Pat. Nos. 4,381,918 and 4,392, 828 to Ehmnford there is disclosed a filler comprising porous inorganic particles which are completely or partially impregnated with a resin material. The porous inorganic particles are formed by heating inorganic fibers under pressure to fuse the fibers at their points of contact, thereby forming a rigid three-dimensional network of inorganic fibers. Fused-fibrous filler compositions are also disclosed in U.S. Pat. No. 5,621,035 to Lyles et al. Such fillers comprise silica fibers together with either alumina or aluminosilicate fibers which are fused in the presence of a fusion source such as boron nitride. The presence of boron lowers the melting point of the fibers sufficiently to allow formation of a porous, interconnected network. The network is then ground to particles having a size of about 180 microns, and used as fillers in dental composites.

Unfortunately, use of the fused-fibrous filler compositions disclosed in the Ehrnford and Lyles patents requires multiple steps and extensive preparation time. Accordingly, there is a need in the dental arts to develop a dental resin composite which is similar to or approaching to dental amalgam alloys in handling characteristics, physical properties, and applications without the drawbacks and deficiencies associated with dental amalgam alloys, and without the multiple preparation steps required for fused-fibrous compositions.

SUMMARY OF THE INVENTION

The above-described and other problems and deficiencies of the prior art are overcome or alleviated by the composition and method of manufacture of the present invention, comprising ground, densified, embrittled glass fiber fillers and a polymeric matrix. In accordance with the present invention, glass fibers are densified and embrittled by heating the glass fibers at an effective temperature substantially below the softening point of the glass fibers such that the glass fibers are densified and embrittled, which as used herein excludes fusing or melting together. The densified, embrittled fibers are then ground to a fibrous particle size preferably less than about 80 microns ($\mu$m). The ground, densified, embrittled glass fibers of the present invention are preferably used as a filler component of a dental composite, being present in the range from about 5% to about 95% by weight of the total composition, depending upon the use made of the polymerized composition. In addition to the ground, densified, embrittled glass fibers, the polymeric matrix may further comprise other fillers known in the art.

The resulting dental composite exhibits handling characteristics similar to or approaching that of dental amalgam, and is particularly a suitable substitute filling for amalgam without the alleged health hazard concerns. The above-discussed and other features and advantages of the present invention will be appreciated and understood by those skilled in the art from the following detailed description and drawings.

BRIEF DESCRIPTION OF THE DRAWINGS

For the purpose of illustrating the invention, there are shown in the drawing forms which are presently preferred; it being understood, however, that this invention is not limited to the precise arrangements and instrumentalities shown. Referring now to the drawings wherein like elements are numbered alike in the several FIGURES.

DETAILED DESCRIPTION OF THE INVENTION

Figure 1:
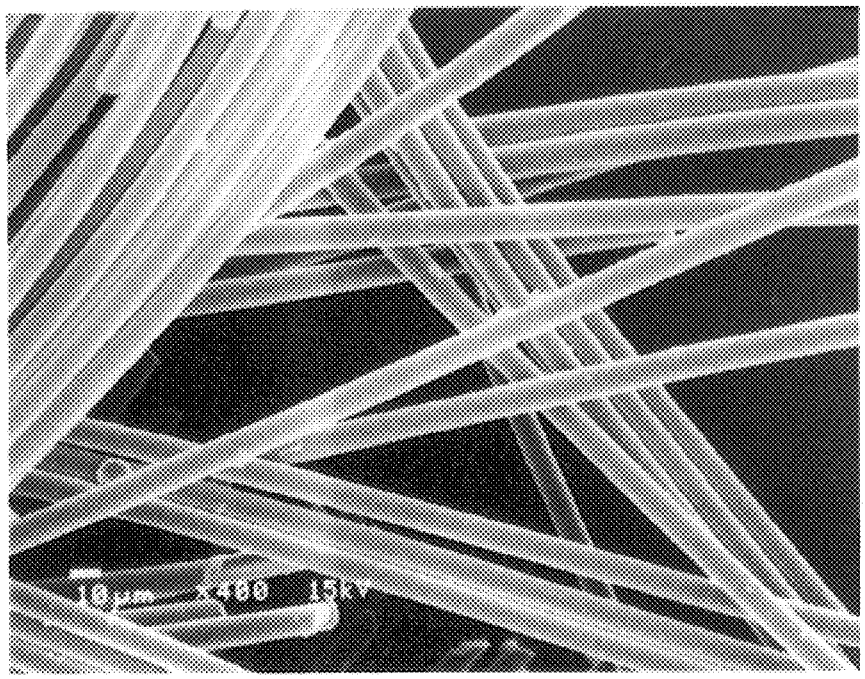
FIG. 1 is a photomicrograph of glass fibers before heating the glass fibers in accordance with the present invention.

The present invention is a dental restoration material comprising a polymeric matrix and ground, densified, embrittled glass fibers, wherein the glass fibers have been densified and embrittled by heating the glass fibers at a temperature substantially below the softening point of the glass fibers. Glass fibers as ordinarily provided by the manufacturer tend to be less dense, and somewhat flexible, that is, capable of being bent without breaking. As used herein, the term "densify" means to cause the fibers to become more dense, that is, to shrink in volume with practically no fusing or melting together of the fibers at their points of contact. "Embrittled" as used herein means to cause the fibers to become more prone to breakage upon the application of force, with practically no fusing or melting together of the fibers at their points of contact. Further as used herein, the term "substantially below" refers to a temperature effective to densify and embrittle the glass fibers, but not to fuse or melt the glass fibers together at their points of contact. The densified, embrittled glass particles are then cooled and ground to a particle size less than about 80 microns according to grinding methods known in the art.

A number of glass compositions are suitable for use in the practice of the present invention, including but not being limited to known glasses listed in the Table below. A preferred glass composition is fibers comprising S-2 GLASS®, which is commercially available from Owens Corning. Such fibers have diameters of about 10 microns.

| Oxide* | A-Glass | C-Glass | D-Glass | E-Glass | ECR-Glass ® | AR-Glass | R-Glass | S-2 Glass ® |
|---|---|---|---|---|---|---|---|---|
| $SiO_2$ | 63–72 | 64–68 | 72–75 | 52–56 | 54–62 | 55–75 | 55–65 | 64–66 |
| $Al_2O_3$ | 0–6 | 3–5 | 0–1 | 12–16 | 9–15 | 0–5 | 15–30 | 24–25 |
| $B_2O_3$ | 0–6 | 4–6 | 21–24 | 5–10 | | 0–8 | | |
| CaO | 6–10 | 11–15 | 0–1 | 16–25 | 17–25 | 1–10 | 9–25 | 0–0.1 |
| MgO | 0–4 | 2–4 | | 0–5 | 0–4 | | 3–8 | 9.5–10 |
| ZnO | | | | | 2–5 | | | |
| BaO | | 0–1 | | | | | | |
| $Li_2O$ | | | | | | 0–1.5 | | |
| $Na_2O$ + $K_2O$ | 14–16 | 7–10 | 0–4 | 0–2 | 0–2 | 11–21 | 0–1 | 0–0.2 |
| $TiO_2$ | 0–0.6 | | | 0–1.5 | 0–4 | 0–12 | | |
| $ZrO_2$ | | | | | | 1–18 | | |
| $Fe_2O_3$ | 0–0.5 | 0–0.8 | 0–0.3 | 0–0.8 | 0–0.8 | 0–5 | | 0–0.1 |
| $F_2$ | 0–0.4 | | | 0–1 | | 0–5 | 0–0.3 | |
| Softening point, ° C. | 705 | 750 | 771 | 846 | 882 | 773 | 952 | 1056 |

*Percent by weight

In the practice of the present invention, glass fibers are densified and embrittled by heating at a temperature substantially below the softening point of the glass for a time effective to densify the glass. Such temperature and time are interdependent, and are empirically determined, based on the composition (and thus the softening point) of the glass. Higher temperatures will generally result in shorter times. The temperature must be high enough to effect densification and embrittlement, but not so high as to cause fusion, while the time of heating must be such as to allow even heating, but again, no fusion of the fibers at the chosen temperature.

In a preferred embodiment, at atmospheric pressure, the temperature is at least about 75° C. below the softening point of the glass, and more preferably, at atmospheric pressure, the temperature is between about 100° C. and about 140° C. below the softening point of the glass. S-2 GLASS®, for example, has a softening point of 1056° C. In accordance with the present invention, the S-2 GLASS® fibers are preferably heated at a temperature between about 920° C. to about 950° C. for about 0.5 to 4 hours, a time period effective to densify the glass fibers but not fuse or melt the glass fibers together. In a particularly preferred embodiment, the S-2 GLASS® fibers are heated at a temperature of about 940° C. for about 2 hours.

After densification, the glass fibers are ground to a size suitable for use as a filler in a dental restoration, preferably below about 100 microns. As used herein, grinding refers to any known methods for size reduction, including reduction to spherical or fiber form. To obtain the desired amalgam "feel", the particles are ground to a size of less than about 80 microns. At this size, the particles generally retain a fibrous form, that is, a length greater than their diameter.

The polymeric matrix portion of the dental composite is selected from those known in the art of dental materials, including but not being limited to expandable monomers, liquid crystal monomers, ring-opening monomers, polyamides, acrylates, polyesters, polyolefins, polyimides, polyarylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like. These polymeric matrices are derived from curing polymeric matrix precursor compositions. Such precursor compositions are well-known in the art, and may be formulated as one-part, two-part, or other compositions, depending on the components.

Preferred materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine and application Ser. No. 60/036,184 filed on Jan. 17, 1997, all of which are herein incorporated by reference in their entirety. Especially preferred methacrylate monomers include the condensation product of bisphenol A and glycidyl methacrylate, 2,2'-bis [4-(3-methacryloxy-2-hydroxy propoxy)-phenyl] propane (hereinafter abbreviated BIS-GMA), the condensation product of ethoxylated bisphenol A and glycidyl methacrylate, (hereinafter EBPA-DMA), and the condensation product of 2 parts hydroxymethylmethacrylate and 1 part triethylene glycol bis (chloroformate) (hereinafter PCDMA). Polyurethane dimethacrylates (hereinafter abbreviated to PUDMA) are also commonly-used principal polymers suitable for use in the present invention.

The polymeric matrix precursor composition may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethyl methacrylate, 1,6-hexanediol dimethacrylate, and 2-hydroxypropyl methacrylate; glyceryl dimethacrylate; ethyleneglycol methacrylates, including ethyleneglycol methacrylate, diethyleneglycol dimethacrylate, triethyleneglycol dimethacrylate and tetraethyleneglycol dimethacrylate; or disocyanates, such as 1,6-hexamethylene disocyanate. Triethyleneglycol dimethacrylate (TEGDMA) is particularly preferred for use in the present invention.

The polymeric matrix precursor composition typically includes polymerization initiators, polymerization accelerators, ultra-violet light absorbers, anti-oxidants, fluorescent whitening agents, and other additives well known in the art. The polymer matrices may be visible light curing, self-curing, dual curing, and vacuum-, heat-, and pressure-curable compositions as well as any combination thereof Visible light curable compositions employ light-sensitive compounds such as benzil diketones, and in particular, dl-camphorquinone in amounts ranging from about 0.05 to 0.5 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y. in amounts ranging from about 0.05 to about 5.0 weight percent.

In the self curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions include, in addition to the monomeric components, a heat cure initiator such as benzoyl peroxide, 1,1'-azobis (cyclohexanecarbonitrile), or other suitable free radical initiators. Particularly suitable free radical initiators are lauroyl peroxide, tributyl hydroperoxide, AIBN and, more particularly benzoyl peroxide or 1,1'-azobis (cyclohexanecarbonitrile).

The total amount of filler is determined by the specific function of the filled materials, being in the range from about 5 to 95% by weight of the total composite composition. Preferably, the composites of the present invention may also include other inorganic and/or organic fillers or a mixtures thereof currently used in dental restorative materials. When used as a direct filling material, the desired amalgam feel is obtained by using about 10 to about 60% by weight of ground, densified, embrittled glass fiber and from about 30 to about 80% by weight of other filler, for example barium borosilicate. A preferred composition comprises about 15% by weight of a resin mixture comprising EBP-DMA and PCDMA in a ratio of 70:30 by weight, about 35% by weight of ground, densified, embrittled glass filler, and about 50% by weight of barium borosilicate filler.

Examples of other suitable filling materials include, but are not limited to, silica, silicate glass, quartz, barium silicate, strontium silicate, barium borosilicate, strontium borosilicate, borosilicate, lithium silicate, amorphous silica, ammoniated or deammoniated calcium phosphate -and alumina, zirconia, tin oxide and titania. Suitable fillers for dental filling-type materials prepared in accordance with this invention are those having a particle size ranging from about 0.1–5.0 μm with a silicate colloid of 0.001 to about 0.07 microns and prepared by a series of milling steps comprising wet milling in an aqueous medium, surface etch milling and silanizing milling in a silane solution. Some of the aforementioned inorganic filing materials are disclosed in U.S. Pat. Nos. 4,544,359 and 4,547,531, pertinent portions of which are incorporated herein by reference.

Figure 2:
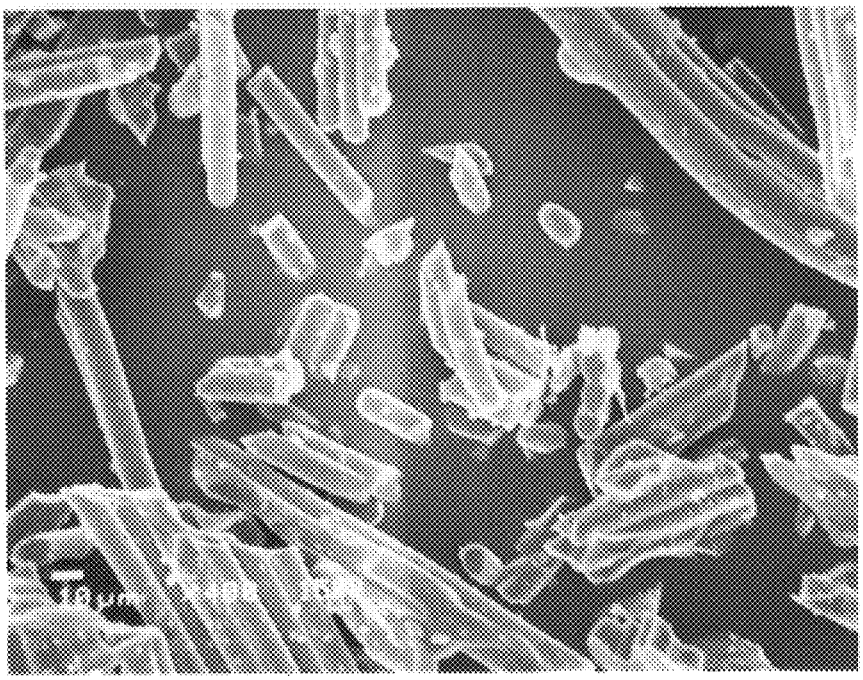
FIG. 2 is a photomicrograph of the densified, embrittled glass fibers after the glass fibers have been heated substantially below the softening point of the glass fibers.
Figure 3A:
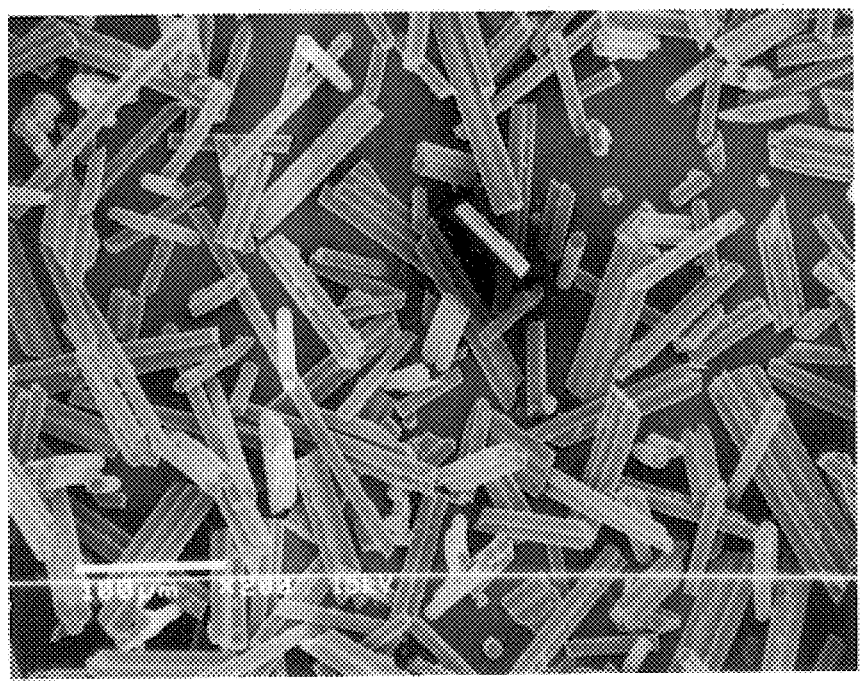
FIGS. 3A and 3B are photomicrographs at an (A) 10 micron and (B) 100 micron scale of the densified, embrittled glass fibers after grinding to a particle size of less than about 80 $\mu$m.
Figure 3B:
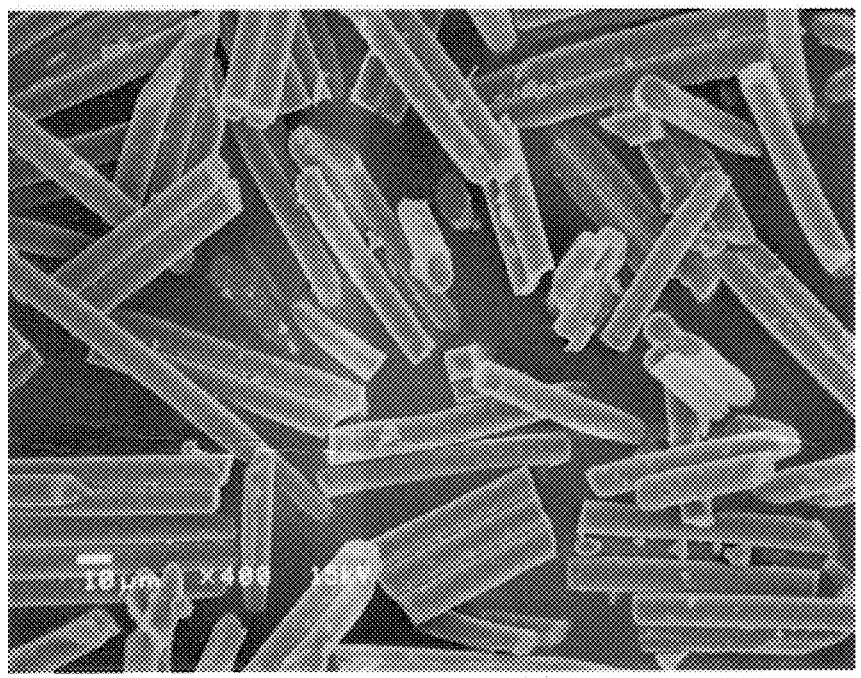

Referring now to the drawings wherein like numerals indicate like elements, FIG. 1 is a photomicrograph of S-2® glass fibers 10 before the fibers have been densified and embrittled. FIG. 2 illustrates S-2® glass fibers 12 which have been densified and embrittled by heating the glass fibers at a temperature substantially below the softening point of the glass fibers in accordance with the present invention. The glass fibers 12 are not fused or melted. FIGS. 3A and 3B are photomicrographs illustrating the densified, embrittled glass fibers 14 of the present invention after grinding.

The dental composites of the present invention provide improved handling characteristics, physical properties, and provide an attractive substitute to dental amalgam alloys as direct filling materials. The composites allow use of mechanical packing and condensing with its attendant advantages. The ground, densified, embrittled glass fiber filler of the present invention may further be utilized in numerous other applications in the practice of dentistry, including periodontal splitting, tooth replacement, tooth stabilization, bridge manufacture, and the like. All of these will not be described herein, as such dental operations are well known to those practicing dentistry, i.e. those of ordinary skill in the art.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method of making a composition for forming a dental composite material, comprising heating glass fibers at a temperature between about 100° C. and 140° C. below the softening point of the glass for a period of time effective to densify and embrittle the glass fibers;

cooling, the densified, embrittled glass fibers;

grinding the densified, embrittled glass fibers to form ground, densified, embrittled glass particles; and incorporating the ground, densified, embrittled glass particles into a polymeric matrix precursor composition to form a dental composite.

2. The method of claim 1, where the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

3. The method of claim 2, wherein the temperature is in the range between about 920° C. and about 950° C.

4. The method of claim 2, wherein the temperature is about 940° C.

5. The method of claim 1, wherein the ground, densified, embrittled glass particles have an average particle size of less than about 80 microns.

6. The method of claim 1, wherein the polymeric matrix precursor composition comprises at least one acrylate or methacrylate monomer.

7. The method of claim 1, wherein the ground, densified, embrittled glass particles comprise from about 5% to about 80% by weight of the total composition.

8. The method of claim 7, wherein the ground, densified, embrittled glass particles comprise about 35% by weight of the total composition.

9. The method of claim 1, wherein the composition comprises at least one additional filler material.

10. The method of claim 9, wherein the filler material is at least one of silica, silicate glass, quartz, barium silicate, strontium silicate, barium borosilicate, borosilicate, lithium silicate, amorphous silica, ammoniated or deammoniated calcium phosphate, alumina, zirconia, tin oxide or titania.

11. The method of claim 10, wherein the at least one additional filler material is barium borosilicate, comprising between about 5% to about 85% by weight of the total composition.

12. A dental composite composition for forming a dental restoration comprising ground, densified, embrittled glass particles, wherein the particles are derived from glass fibers heated at a temperature between about 100° C. and 140° C. below the softening point of the glass fibers for a period of time effective to densify and embrittle the glass fibers, the densified, embrittled glass fibers being subsequently ground; and a polymeric matrix precursor composition.

13. The composite of claim 12, wherein the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

14. The composite of claim 13, wherein the temperature is in the range between about 920° and about 950° C.

15. The composite of claim 14, wherein the temperature is about 940° C.

16. The composite of claim 12, wherein the ground, densified, embrittled glass particles have an average particle size of less than about 80 microns.

17. The composite of claim 13, wherein the polymeric matrix precursor composition comprises at least one acrylate or methacrylate monomer.

18. The composite of claim 12, wherein the ground, densified, embrittled glass particles comprise from about 5% to about 80% by weight of the total composite composition.

19. The composite of claim 18, wherein the ground, densified, embrittled glass particles comprise about 35% by weight of the total composite, composition.

20. The composite of claim 12, wherein the dental composite comprises at least one additional filler material.

21. The composite of claim 18, wherein the at least one additional filler material is at least one of silica, silicate glass, quartz, barium silicate, strontium silicate, barium borosilicate, borosilicate, lithium silicate, amorphous silica, ammoniated or deammoniated calcium phosphate, alumina, zirconia, tin oxide or titania.

22. The composite of claim 21, wherein the at least one additional filler material is barium borosilicate, comprising between about 5% to about 85% by weight of the total composite composition.

23. A dental restoration comprising ground, densified, embrittled glass particles, wherein the particles are derived from glass fibers heated at a temperature about 100° C. and 140° C. below the softening point of the glass fibers for a period of time effective to densify and embrittle the glass fibers, the densified, embrittled glass fibers being subsequently ground; and a cured polymeric matrix precursor composition.

24. The dental restoration of claim 23, wherein
the glass fibers have a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$.

25. The dental restoration of claim 24, wherein
the temperature is in the range between about 920° and 950° C.

26. The dental restoration of claim 24, wherein
the temperature is about 940° C.

27. The dental restoration of claim 23, wherein
the ground, densified, embrittled glass particles have an average particle size of less than about 80 microns.

28. The dental restoration of claim 23, wherein
the polymeric matrix precursor composition comprises at least one acrylate or methacrylate monomer.

29. The dental restoration of claim 23, wherein
the ground, densified, embrittled glass particles comprise from about 5% to about 85% by weight of the total composite composition.

30. The dental restoration of claim 29, wherein
the ground, densified, embrittled glass particles comprise about 35% by weight of the total composite composition.

31. The dental restoration of claim 23, wherein
the dental composite comprises at least one additional filler material.

32. The dental restoration of claim 31, wherein
the filler material is at least one of silica, silicate glass, quartz, barium silicate, strontium silicate, barium borosilicate, borosilicate, lithium silicate, amorphous silica, ammoniated or deammoniated calcium phosphate, alumina, zirconia, tin oxide or titania.

33. The dental restoration of claim 32, wherein
the at least one additional filler material is barium borosilicate, comprising between about 5% to about 85% by weight of the total composite composition.

34. A method of making a composition for forming a dental composite material, comprising:
heating glass fibers having a composition comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$ at a temperature between about 920° C. and 950° C. for a period of time effective to density and embrittle the glass fibers;
cooling the densified, embrittled glass fibers;
grinding the densified, embrittled glass fibers to form ground, densified, embrittled glass particles; and
incorporating the ground, densified, embrittled glass particles into a polymeric matrix precursor composition to form a dental composite.

35. The method of claim 34, wherein
the temperature is about 940° C.

36. The method of claim 34, wherein
the ground, densified, embrittled glass particles have an average particle size of less than about 80 microns.

37. The method of claim 34, wherein
the ground, densified, embrittled glass particles comprise from about 5% to about 80% by weight of the total composition.

38. The method of claim 34, wherein
the composition comprises at least one additional filler material.

39. A dental composite composition for forming a dental restoration comprising
ground, densified, embrittled glass particles, wherein the particles are derived from glass fibers comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$ heated at a temperature between about 920° C. and 950° C. for a period of time effective to density the glass fibers, the densified, embrittled glass fibers being subsequently ground; and
a polymeric matrix precursor composition.

40. The composite of claim 39, wherein
the temperature is about 940° C.

41. The composite of claim 39, wherein
the ground, densified, embrittled glass particles have an average particle size of less than about 80 microns.

42. The composite of claim 39, wherein
the ground, densified, embrittled glass particles comprise from about 5% to about 80% by weight of the total composite composition.

43. The composite of claim 39, wherein
the dental composite comprises at least one additional filler material.

44. A dental restoration comprising
ground, densified, embrittled glass particles, wherein the particles are derived from glass fibers comprising about 64–66% $SiO_2$, 24–25% $Al_2O_3$, 0–0.1% CaO, 9.5–10% MgO, 0–0.2% $Na_2O+K_2O$, and 0–0.1% $Fe_2O_3$ heated at a temperature between about 920° C. and about 950° C. for a period of time effective to densify the glass fibers, the densified, embrittled glass fibers being subsequently ground; and
a cured polymeric matrix precursor composition.

45. The dental restoration of claim 44, wherein
the temperature is about 940° C.

46. The dental restoration of claim 44, wherein
the ground, densified, embrittled glass particles have an average particle size of less than about 80 microns.

47. The dental restoration of claim 44, wherein
the ground, densified, embrittled glass particles comprise from about 5% to about 85% by weight of the total composite composition.

48. The dental restoration of claim 44, wherein
the dental composite comprises at least one additional filler material.

* * * * *

UNITED STATES PATENT AND TRADEMARK OFFICE
CERTIFICATE OF CORRECTION

PATENT NO.     : 6,013,694
DATED          : January 11, 2000
INVENTOR(S)    : Jia et al.

It is certified that error appears in the above-identified patent and that said Letters Patent is hereby corrected as shown below:

Column 1,
Line 8, after "thereof" insert -- . -- (period),
Line 30, after "therfor", insert -- . -- (period)
Line 60, after "include" delete "fused" and insert therefor -- fumed --
Line 63, after "thereof", insert -- . -- (period)

Column 2,
Line 27, after "patents" delete "is discloses" and insert therefor -- disclose --
Line 34, after "to" delete "Ehmnford" and insert therefor -- Ehrnford --

Column 5,
Line 55, after "or" delete "disocyanates" and insert therefor -- diisocyanates --
Line 56, after "hexamethylene" delete "disocyanate" and insert therefor
-- diisocyanate --
Line 65, after "thereof", insert -- . -- (period)

Column 6,
Line 5, after "resin" delete "form" and insert therefor -- from --
Line 51, after "phosphate" delete "-and" and insert therefor -- and --

Column 8,
Line 30, after "claim" delete "13" and insert therefor -- 12 --
Line 44, after "claim" delete "18" and insert therefor -- 20 --

Column 9,
Line 43, after "to" delete "density" and insert therefor -- densify --

UNITED STATES PATENT AND TRADEMARK OFFICE
CERTIFICATE OF CORRECTION

PATENT NO. : 6,013,694
DATED : January 11, 2000
INVENTOR(S) : Jia et al.

It is certified that error appears in the above-identified patent and that said Letters Patent is hereby corrected as shown below:

<u>Column 10,</u>
Line 15, after "to" delete "density" and insert therefor -- densify --

Signed and Sealed this

Seventeenth Day of February, 2004

JON W. DUDAS
*Acting Director of the United States Patent and Trademark Office*